United States Patent [19]

Pawliszyn

[11] Patent Number: 5,492,838
[45] Date of Patent: Feb. 20, 1996

[54] PROCESS AND DEVICE FOR CONTINUOUS EXTRACTION AND ANALYSIS OF FLUID USING MEMBRANE

[76] Inventor: Janusz B. Pawliszyn, 383 Dunvegan Drive, Waterloo, Ontario, Canada, N2K 1W7

[21] Appl. No.: 348,864

[22] Filed: Nov. 28, 1994

Related U.S. Application Data

[63] Continuation-in-part of Ser. No. 46,875, Apr. 13, 1993, abandoned.

[30] Foreign Application Priority Data

Apr. 15, 1992 [GB] United Kingdom ............. 9208313

[51] Int. Cl.$^6$ ............. G01N 21/64; G01N 33/52; G01N 1/18
[52] U.S. Cl. ............. 436/178; 422/68.1; 422/70; 422/256; 210/175; 210/321.8; 210/321.75
[58] Field of Search .............. 422/68.1, 69, 70, 422/82.02, 82.05, 256; 436/178; 210/321.8, 175, 321.75

[56] References Cited

U.S. PATENT DOCUMENTS 5,094,817  3/1992  Aoki et al. ............. 422/68.1
5,133,859  7/1992  Frank et al. ............. 436/178

*Primary Examiner*—Lyle A. Alexander
*Attorney, Agent, or Firm*—Daryl W. Schnurr

[57] ABSTRACT

A process and a device for the continuous extraction and analysis of chemical substances from solute fluid using membrane is characterized by passing solute fluid 14 through housing 20 on one side of a semipermeable structure 19 and simultaneously passing extracting fluid 11 through the housing on the other side of the semipermeable membrane structure. Substances passing from solute fluid through the semipermeable membrane structure into the extracting fluid are delivered by the extracting fluid as carrier, into a sorbing phase 27. Cooling 28 and heating 24 of the sorbing phase allows substances to be concentrated and detected by detector 50 and to be continuously monitored. Extracting fluid may be a gas or a pressurized dense gas. Extraction using pressurized dense gas and membrane is achieved by maintaining the pressure of the solute fluid and the pressurized dense gas within a high pressure housing substantially equal. Previously, solute fluids were analyzed using batch processes with liquid-liquid extraction, extraction cartridges or purge and trap. Continuous extraction and analysis using membranes eliminates the use of organic solvents and provides inexpensive and continuous monitoring of volatile, semi-volatile, non-volatile and polar compounds in water and other fluids.

17 Claims, 16 Drawing Sheets

|         | DMP    | DCP    |
|---------|--------|--------|
| Trial 1 | 72.69% | 68.57% |
| Trial 2 | 69.18% | 64.52% |
| Trial 3 | 81.36% | 73.48% |
| Average | 74.41% | 68.85% |
| RSD     | 8.43%  | 6.52%  |

PROCESS AND DEVICE FOR CONTINUOUS EXTRACTION AND ANALYSIS OF FLUID USING MEMBRANE

This is a continuation-in-part application of Application Ser. No. 08/046,875 filed Apr. 13, 1993 now abandoned.

BACKGROUND OF THE INVENTION

1. Field of the Invention

This invention relates to a process and device for the continuous extraction and analysis of chemical substances from fluid using membranes directly interfaced to an analytical device and extraction of semi-volatile, non-volatile and polar substances from fluid using pressurized dense gas.

2. Description of the Prior Art

The removal of substances from fluid such as water is important for a number of reasons. Of particular interest are organic substances, since many are known to be toxic or carcinogenic or may also contribute to undesirable properties, such as poor odour or taste.

Such substances may be removed from water in order to identify and quantitate the substances to protect the public. Secondly, they may be monitored and possibly removed from water prior to the water being used for some manufacturing processes, for example, for some pharmaceutical and for some beverage production. Thirdly, it is important to remove organic substances from water for water remediation.

In general, the organic substances of interest in water are divided into three classes; volatile, semi-volatile and non-volatile. Polar substances in these three groups are the most difficult to deal with because of their affinity to water.

Organic substances, present as pollutants of interest in many water samples, are typically found in part per million and part per billion levels. Presently, in the analysis of organic substances from water, there are at least two steps. First is the extraction of the substances from the water and second is the analysis of the extract. Methods of analysis such as gas chromatography and gas chromatography-mass spectrometry are very rapid, sensitive and selective. Current extraction methods, on the other hand, are tedious, slow and often involve the use of considerable amounts of organic solvent. Loss of sample, reducing the accuracy of the method, is common.

Direct injection of the matrix containing target analytes eliminates the extraction step and the use of organic solvent, but has poor sensitivity and suffers from many interferences.

Extraction techniques include static headspace sampling, purge and trap, solid phase extraction, liquid/liquid extraction and distillation. Static headspace is not a sensitive technique and is not suitable for non-volatile substances. Purge and trap is widely used for volatiles, however, it suffers from many problems due to water vapor carry-over. Since cryogenic cooling is usually required to concentrate the analytes, freezing of the water is a problem. Water also causes interference with the chromatographic analysis and reduces column lifetimes. Foaming of the sample during purging in purge-trap methods can also be a problem. Automated equipment for multiple samples is expensive, complicated and prone to problems such as leaks. Solid phase extraction is efficient but still requires the use of organic solvent. Solid phase extraction cartridges are typically used only once for one sample and are then disposed. This generates solid waste. Liquid-liquid extraction is widely used but requires the separation of the phases following extraction. This can result in loss of sample and is labour intensive. The most serious problems with liquid-liquid extraction, are due to the large amounts of organic solvents required for extraction. Solvent costs are high and solvent use presents health risks as well as being an environmental hazard. Disposal costs for waste solvent are high. There is a great desire to reduce solvent useage in laboratories, however this has been difficult without acceptable alternative methods being available. Distillation is not an energy efficient method of extraction and is labour intensive. Loss of volatile substances often occurs with distillation.

In each of these extraction techniques, the method of analysis must still be performed as a separate operation. This is inefficient and introduces many types of errors into the analytical result. Continuous analysis of volatile, semi-volatile and non-volatile organic substances in water is not possible using batch extraction and analysis techniques.

Considerable effort has been expended developing methods for the analysis of volatile, semi-volatile and non-volatile organic pollutants in water. For example, in the United States, the Environmental Protection Agency (EPA) Priority Pollutants designated in Method of Organic Chemical Analysis of Municipal and Industrial Wastewater EPA-600/4-83-057 ( US EPA, Cinninnati, Ohio ) are analyzed by methods described in the Federal Register, Testing Methods for Evaluating Solid Waste, SW-846, 2nd Edition, US EPA Office of Solid Waste and Emergency Response. Industries in the United States are required to use these methods both in evaluating their wastewater and in applying for National Pollution Discharge Permits. Other countries, for example, Canada, Germany and Japan have similar established methods or are in the process of developing comparable methods for these same requirements. Organic pollutants normally are present in parts per billion or lower concentrations in wastewater. Using EPA methods, to achieve required sensitivities, analytes must be concentrated prior to analysis. All EPA wastewater methods are batch methods, involving separate sampling procedures, preconcentration and possibly cleanup, and finally, analysis, which is usually by gas chromatography or gas chromatography-mass spectrometry. Sample preconcentration is by purge and trap or solvent extraction. For volatile compounds, for example EPA Methods 601, 602 and 603 which are purge and trap, loss of volatile substances between sampling and analysis can occur. All other methods, for semi-volatile and non-volatile compounds specify liquid-liquid extraction using organic solvents. For example, Method 625, widely used for non-volatile pollutants, requires a preconcentration step using 300 ml methylene chloride per litre of water sample followed by evaporation to 2 ml. There is considerable concern about the amount of organic solvent required for semi-volatile and non-volatile extractions. Due to the expense involved in these methods and the batch sampling required, continuous analysis of wastewater streams for monitoring of low level priority pollutants is not practical. Interpretation of results and conclusions regarding the nature and sources of priority pollutants is therefore difficult. Separate sampling and analysis processes add greatly to the expense. Necessarily, the sample taken for analysis is a discrete sample, representing the condition of the wastewater at only one point in time. Any useful information about changes in the wastewater discharge must therefore involve expensive repetitive sampling and analysis. Alternatively, the sample may be an averaged sample, taken using specialized and expensive time-based sampling devices. However, this does not provide any information about pollutant flux.

Computers may be used to collect and analyze data on EPA priority pollutant sources, however, due to the lack of availability of an inexpensive method to generate continuous analysis data from these sources, it is impossible or very expensive to attempt to fully characterize pollutant sources, especially with respect to rapid changes in pollutant levels.

The use of semipermeable structures such as membranes can provide efficient means of extraction of organic substances from a fluid. Membranes are available in a variety of forms and shapes. Flat sheets are often used, especially for dialysis, however, the hollow fibre is a more useful geometry. A larger surface area per volume is obtained and hence more efficient extraction is possible. There are two geometries used with the hollow fibre membrane. One is referred to as the flow-over configuration. In this configuration, the stripping media flows through the fibre while the feed solution is pumped around the exterior of the fibre. The second geometry is the flow-through configuration. In this type of set-up, the stripping media flows around the exterior of the fibre while the feed solution is pumped through the fibre. The flow-through configuration results in higher linear velocities and improved surface area per volume ratio.

Hollow fibre membrane has been used for analytical and for process applications. In analytical applications, hollow fibre membranes have been studied as a method of direct sample introduction into a mass spectrometer. This system is being studied in analytical chemistry as well as in biotechnology and microbiology. Membrane introduction mass spectrometry has allowed continuous monitoring of chemical or biochemical reactions. However, in this situation, vacuum is used to strip the analytes from the membrane and there is no means of concentrating the analytes. Sensitivity is therefore limited by this technique.

Gas chromatography is a more prevalent and less expensive technique than direct mass spectrometry. However, in all prior methods using membrane, the continuous extraction and continuous analysis of organic substances in aqueous fluid using gas chromatography has not been possible.

Multiplex gas chromatographic analysis has been used to permit continuous monitoring of gaseous components with rapidly changing concentrations. It has also proven very useful for trace analysis and eliminates the need for a preconcentration step. Multiplex gas chromatographic analysis of organic substances in water would permit continuous measurement with enhanced sensitivity. This has not been possible, however, because of the interference effect of the water on measurement.

Pressurized dense gases such as supercritical fluid have been shown to effectively extract non-volatile, semi-volatile and polar substances from liquid and solid matrices. This is due to the strong solvating properties of the supercritical fluid. Carbon dioxide can be used in this application because of it's low critical temperature and pressure. It is commonly selected since it is inexpensive, easily available and non-toxic. However, the use of pressurized dense gas such as supercritical carbon dioxide to remove substances from aqueous samples is very difficult and supercritical fluid extraction methods developed-for extraction of organics from water are very limited. Water dissolves in the carbon dioxide and this causes restrictor freezing and plugging. An indirect supercritical fluid extraction method has been developed using a solid sorbent to transfer analytes from water to the supercritical fluid. However, this method includes three time consuming processes: adsorption, drying, and extraction. Loss of analytes can occur during the drying procedure.

U.S. Pat. No. 4,250,331 (1981) to Shimshick shows that dense gas can remove non-volatile polar substances from aqueous fluid by direct contact between the two phases. However, Shimshick only considered the batch process. In the batch process, the extraction is very slow because of poor contact between the phases. Phase separation is difficult. Batch extraction of larger volumes of sample involves large and expensive high pressure extraction vessels. Large vessels used under supercritical fluid pressure and temperature conditions must be used with extreme caution for safety reasons. In the batch process, continuous extraction or analysis of substances in a stream of the aqueous fluid is not possible.

Dense gases under pressure, such as supercritical fluids are typically produced with pressures in the range from 1,500 psi to 10,000 psi. The use of supercritical fluids therefore has not been considered compatible with membrane, due to the limited ability of semipermeable membrane to withstand such pressures.

SUMMARY OF THE INVENTION

It is an object of the present invention to provide a process and a device for continuous extraction and analysis of substances in solute fluid based on separation using a semipermeable structure. Extracting fluid, which may be a gas or pressurized dense gas, carries substances passing from the solute fluid through a semipermeable structure into the extracting fluid. Substances in extracting fluid, providing carrier, are concentrated by a sorbing phase. Single or multiple pulses of cooling and heating of sorbing phase in a tube connected to a detector provide discrete or continuous analysis of substances extracted from the solute fluid. Pressurized dense gas, such as supercritical fluid carbon dioxide may be used as the extracting fluid and thus allow the extraction and analysis of semi-volatile, non-volatile and polar substances.

A device for carrying out continuous extraction and analysis of substances in a solute fluid has a semipermeable structure enclosed in a housing. The semipermeable structure may be a membrane and the membrane may be a flat sheet membrane, single hollow fibre membrane or multiple arrangement of single hollow fibres or a spiralled membrane. Solute fluid is pumped through the housing on one side of the membrane and extraction fluid is pumped simultaneously through the housing on the other side of the membrane. To increase extraction efficiency a spiralled hollow fibre membrane may be used. Due to the semipermeable nature of the membrane, substances in the solute fluid may pass through the membrane into the extracting fluid. Hydrophobic membrane may be used to substantially exclude the passage of water through the membrane, thus allowing the separation of various organic substances from water. The extracting fluid which may contain substances extracted from the solute fluid acts as carrier, to deliver the extracted substances through tubing containing a sorbing phase directly to an analysis device. The sorbing phase may be the liquid phase in a portion of a gas chromatograph column. Discrete or continuous analysis capabilities are provided by cooling and heating the sorbing phase. A single long cooling cycle may be used to concentrate the extracted substances in the sorbing phase followed by rapid heating. The desorbed substances are directed into a detector such as a flame ionization detector or mass spectrometer detector which provides quantitation and may provide identification. High sensitivity can be achieved by this technique, since substances are substantially concentrated by the sorbing phase before being desorbed into the analysis device.

Cooling and heating may also be a high repetition and random sequence of heating and cooling cycles on a portion of tubing containing sorbent. This provides a series of rapid pulses of desorbed substances which may be analyzed continuously. The signal from the detector is analyzed using a deconvolution technique such as cross-correlation, Fourier transformation or Hadamard transformation to obtain the cross correlogram result providing a continuous analysis capability for the substances extracted from solute fluid.

A benefit of my invention is the elimination of organic solvents from the extraction and analysis procedure. Continuous analysis of analytical samples or process streams may be accomplished, also without the use of organic solvents. The construction of the device is simple and the cost of materials to build the device is very low. For many types of samples, for example, groundwater, a single device will give results corresponding to thousands of batch analyses using conventional techniques. There is little or no maintainence. For samples containing a substantial amount of particulate matter, for example, raw sewage from a water treatment facility, simple inline or offline filtration of the sample may be used, when plugging of the device becomes an issue.

This process provides continuous monitoring capability with enhanced sensitivity for substances extracted from fluid.

A process for continuous extraction and analysis of substances in solute fluid using pressurized dense gas is characterized by installing a semipermeable structure which may be a membrane in a high pressure housing. The membrane may be a sheet membrane, single hollow fibre membrane, multiple arrangement of single hollow fibre membranes or spiralled membrane. The pressure of solute fluid and dense gas under pressure within the housing are mantained substantially equal on starting up the extraction and throughout the extraction. Solute fluid is pumped through the housing on one side of the membrane while dense gas under pressure is simultaneously pumped through the high pressure housing on the other side of the membrane.

The technique increases the contact area between phases, eliminates the necessity of phase separation and can also be designed to be selective by exploiting volatility and solubility properties of organics in dense gases and membrane materials. After extraction, stripped organic substances may be separated from the dense gas phase by lowering the pressure in the system and the dense gas may be recycled.

The method can be used for analytical purposes to enable continuous monitoring of volatile, semi-volatile and non-volatile substances industrial streams and water treatment plants. It can also be applied to industrial process separations for product extraction as well as decontamination of waste water streams.

For analytical purposes, the use of organic solvents, common to other extraction processes for semi-volatile and non-volatile substances, is eliminated, thereby providing a benefit to the environment and to working laboratory personnel. For process streams, the use of organic solvents or adsorbents is eliminated. Organic solvents in process sample treatment are expensive and difficult to dispose of. There is a strong desire to reduce or eliminate organic solvent use in industrial processes. Adsorbents are difficult to reuse and are also difficult to dispose.

A very beneficial application of this method is the continuous extraction and analysis from water and other fluids of important volatile substances such as trihalomethanes using extracting fluid such as nitrogen. The continuous extraction using membranes of semi-volatile, non-volatile and polar substances of interest such organic acids, alcohols, phenols, pesticides, polychlorinated biphenyls, polynuclear aromatic hydrocarbons and dioxins is accomplished using extracting fluid such as supercritical carbon dioxide.

Other applications will be apparent to those skilled in the art.

BRIEF DESCRIPTION OF THE DRAWINGS

FIG. 9-B shows a schematic for continuous extraction of substances in solute fluid using dense gas under pressure and a high pressure membrane module with two pumps.

FIG. 9-C shows a schematic for continuous extraction of substances in solute fluid using dense gas under pressure and a high pressure membrane module with a single pump.

FIG. 10 shows a table of results for the extraction and analysis of polar semi-volatile substances from water using supercritical fluid carbon dioxide and hollow fibre membrane in a high pressure membrane module.

DESCRIPTION OF A PREFERRED
EMBODIMENT

Figure 1:
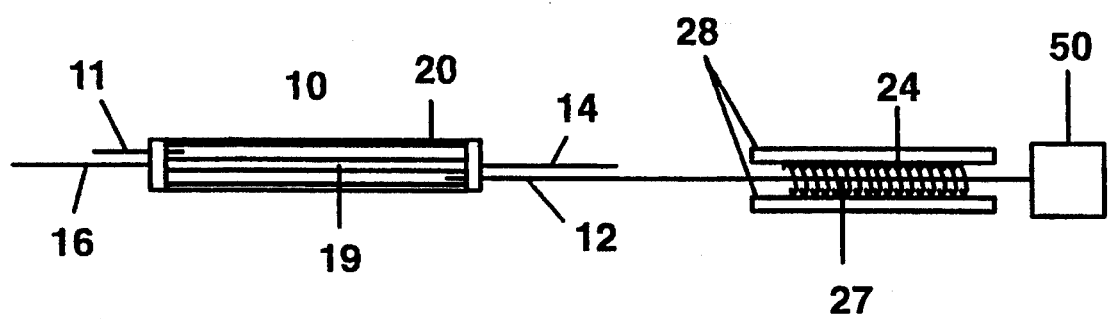
FIG. 1 shows a membrane module with cooling and heating of a sorbing phase.

Referring to FIG. 1, a process for continuous extraction and analysis of substances in fluid is characterized by passing a solute fluid 14 containing substances through housing 20 on one side of semipermeable structure 19 and simultaneously passing extracting fluid 11 through housing 20 on the other side of semipermeable structure 19. Extracting fluid acts as a carrier to deliver substances, passing from solute fluid on one side of the semipermeable structure 19 into extracting fluid on the other side of the semipermeable structure. Extracting fluid, containing extraced substances passes through tube 12 into a sorbing phase 27. By cooling 28 and heating 24, extracted substances in extracting fluid passing through sorbing phase 27 are concentrated. Extracted substance may be delivered to detector 50 following a long cooling cycle and a short heating, to provide maximum sensitivity. Alternatively, rapid and random sequences of cooling and heating of sorbent may be used in a multiplex operation, providing continuous monitoring capability for continuously extracted substances. Solute fluid, substantially purified of extracted substances, exits through connecting tube 16, where it may be collected or recycled back as solute fluid again.

Figure 2A:
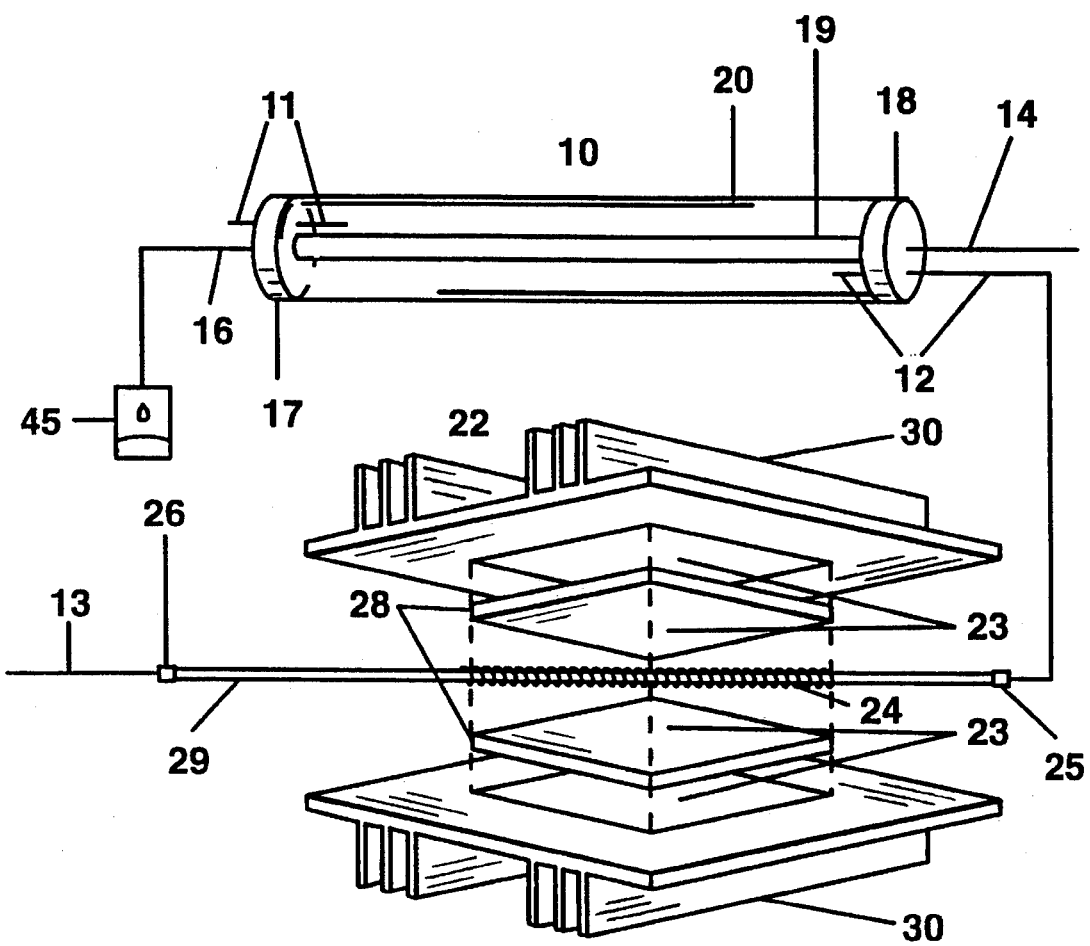
FIG. 2 shows one embodiment of a membrane module with cooling and heating of tubing containing a sorbing phase, in detail.
Figure 2B:
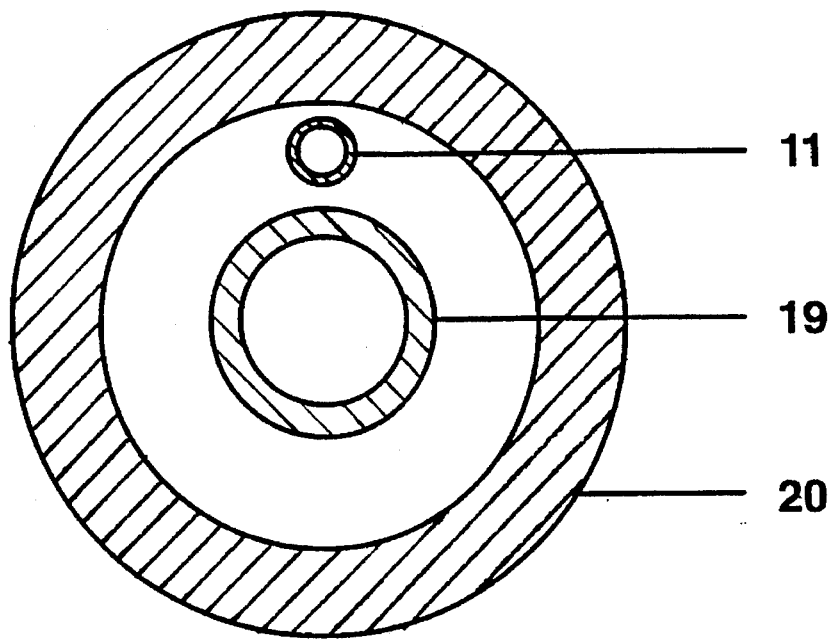
Figure 2C:
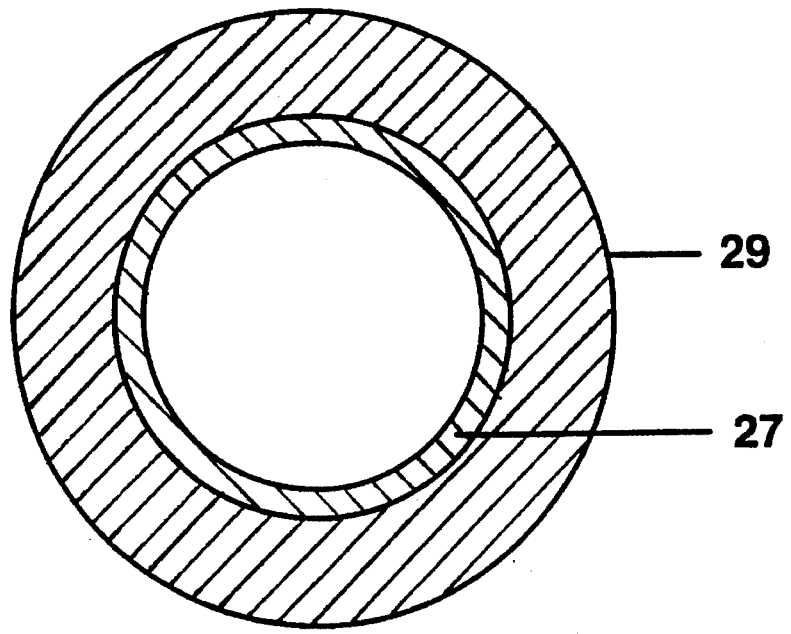

Referring to FIG. 2, in one embodiment, membrane module 10, in detail, is a device consisting of a housing 20, which may be glass or stainless steel for example, enclosing a semipermeable structure 19. Examples of semipermeable structures include membrane such as sheet membrane, hollow fibre membrane and spiralled membrane. One efficient geometry consists of a concentric tube semipermeable structure constituting hollow fibre membrane 19 in a cylindrical tube housing 20. Membrane 19 may be a solid membrane or a porous membrane. A solid membrane such as a silicone membrane will allow the passage of substances by gas-liquid or liquid-liquid diffusion processes whereas a solid membrane such as polypropylene will allow passage of substances by gas-solid or liquid solid diffusion. Hydrophobic membranes are particularly useful for the extraction of substances from water since they do not allow water to cross through the membrane. For example, membrane 19 may be hydrophobic polypropylene hollow fibres (Hoescht Celanese, Charlotte N.C.) or solid silicone fibres (Dow Corning Canada, Mississauga, Ontario). One possible configuration is a straight piece of hollow fibre membrane 19 of 10 cm length inserted through a glass tube housing 20 such that approximately 1 cm of fibre is exposed at each end of glass tube housing 20. To construct a spiralled hollow fibre membrane configuration of membrane 19, a hollow fibre, for example 100 um polypropylene (Hoescht Celanese, Charlotte, N.C.), is wound around a piece of fused silica tubing. The fused silica tubing with the wound hollow fibre is fed through the housing 20 and the fused silica is removed from the centre of the wound hollow fibre leaving the spiralled membrane fibre 19 in housing 20.

Any fluid containing substances to be extracted and analyzed is a solute fluid. Solute fluid may be an analytical sample, a groundwater source such as river water or a well water, an industrial effluent or a process stream in a manufacturing operation or any fluid containing solutes to be extracted and analyzed. Referring further to FIG. 2, seal 17 and seal 18 prevent solute fluid and extracting fluid from leaking out of housing 20 and keep tubes 11, 12, 14 and 16 fixed in the ends of housing 20. For example, five minute cure epoxy (Richmond Supply Ltd., Richmond, B.C.) may be used for seals 17 and 18. Seals 17 and 18 are not required in all embodiments. For example, housing 20 may be constructed to incorporate built-in connections for tubes 11, 12, 14 and 16. For example, a low volume female fitting at each end of housing 20 to accept tubes 11, 12, 14 and 16 and a fitting to accept and support each end of membrane 19 eliminates the need for seals 17 and 18. Solute fluid is pumped through tube 14 which passes through seal 18 into one end of membrane 19. Solute fluid passes through housing 20 on the other side of membrane 19, which may be an interior surface of membrane 19. Extracting fluid which may be a gas or a dense gas is introduced through tube 11 into membrane module 10 between the inner wall of housing 20 and the exterior of membrane 19. Due to the semipermeable nature of membrane 19, substances in solute fluid on one side of membrane 19, which may be an interior of membrane 19, may pass through the membrane and enter extracting fluid on the other side of the membrane. Other substances, including the fluid portion of solute fluid, for example, water, may be excluded from passing across membrane 19 into extracting fluid. Solute fluid, now substantially purified of extracted substances, passes into connecting tube 16 which passes through seal 17. Substantially purified solute fluid from tube 16 can be collected in reservoir 45. Extracting fluid carrying extracted substances enters tube 12 which passes through seal 18 and exits the membrane module 10. Extracting fluid carries extracted substances through tube 12 and into a sorbing phase 27. Sorbing phase 27 may be a solid sorbant such as graphitized carbon or glass beads, a polymeric adsorbent such as styrenedivinylbenzene, a liquid sorbant such as polydimethylsiloxane or a selective sorbant such as silver oxide impregnated silica. In one embodiment, tube 12 carrying extracted substances connects to column tube 13 by fitting 25. In this case, there is no tube 29 or fitting 26 and column 13 extends through thermal modulator 22 and heater 23 is wrapped around column tube 13. For example, tube 13 in this case may be an open tubular capillary column coated with a liquid phase such as polydimethylsiloxane. The liquid phase acts as sorbing phase 27 and also provides chromatographic separation for the substances in extracting fluid. In a second embodiment tube 12 is connected by fitting 25 to a tube 29 containing sorbing phase 27. Tube 29 is connected in this embodiment to tube 13 by fitting 26. Tube 13 may be a gas chromatographic column which provides separation prior to detection. Alternatively, tube 13 connects directly to a detector such as a mass spectrometer and extracted solutes are measured directly, without chromatographic separation.

With further reference to FIG. 2, cooling and heating of sorbing phase 27 provides concentrating and continuous analysis capabilities. One efficient embodiment providing cooling and heating is a thermal modulator 22 consisting of heater 24 which may be a resistive heating wire, wound around fused silica column tube 13, if sorbing phase 27 is the gas chromatographic column phase. For example, a piece of resistor wire 45 ohm and 41 cm length is wound around 6 to 8 cm of the column tube 13. In this embodiment, column tube 13 is connected to extracting fluid tube by fitting 25 while fitting 26 and tube 29 are eliminated. Alternatively, filament heating wire 24 may be wound around tube 29 if tube 29 contains sorbing phase and tube 29 is connected to extracting fluid tube 12 by fitting 25 and column tube 13 is connected to tube 29 using fitting 26. Heater 24 provides heat which is transferred into sorbing phase 27 through column tubing 13 or tube 29. Cooling 28 may be provided by Peltier type thermoelectric wafers 28 on both sides of heater 24. For example, 40 mm× 40 mm×4.7 mm thermoelectric wafers CPI.4-127-10L (Melcor Material and Electronic Products, Trenton, N.J.) are suitable. To maintain cooling efficiencies of thermoelectric wafers 28, aluminum finned heat sinks 30 can be attached to both outside surfaces of thermoelectric wafers 28. Thermal compound 23, for example product 120-8 (Wakefield Engineering Inc, Wakefield, Mass.) can be used to provide efficient heat transfer between sorbing phase 27, tube 13 or tube 29, heater 24, coolers 28 and heat sinks 30.

Figure 3A:
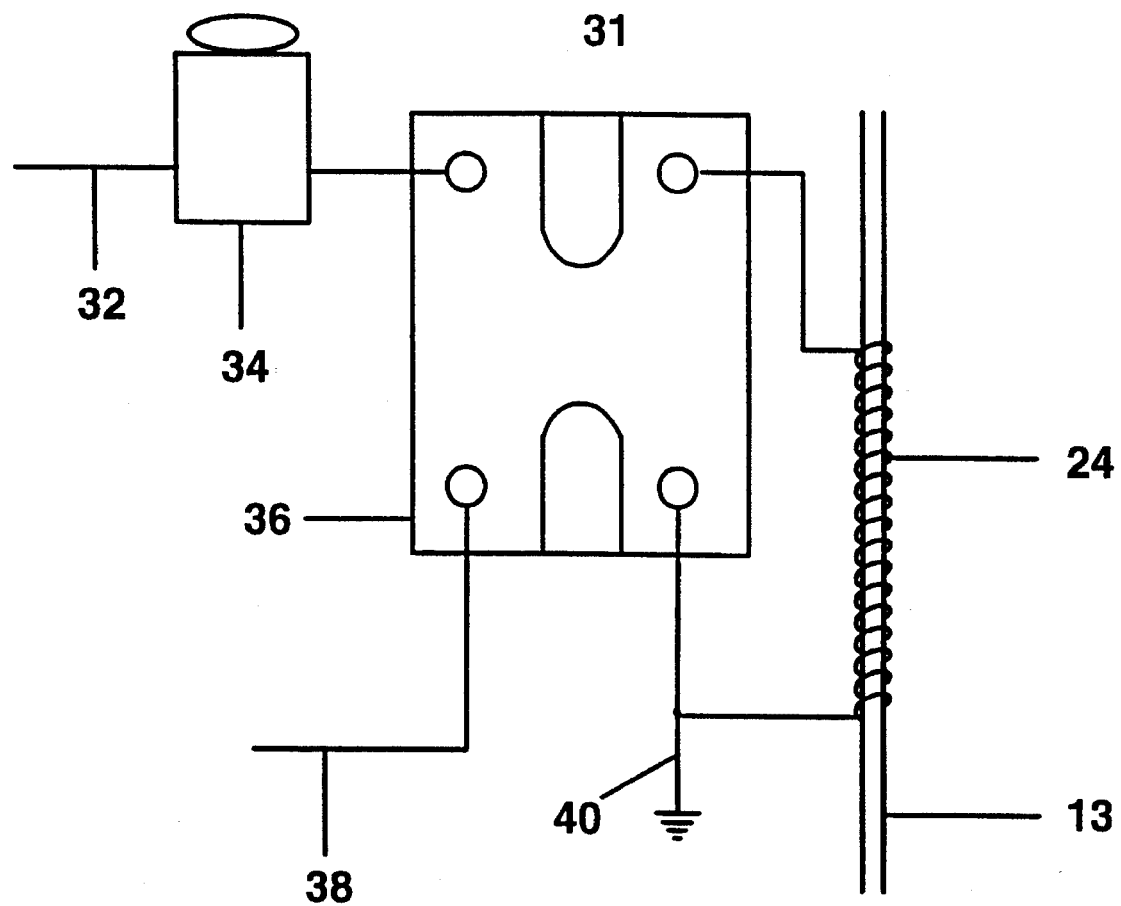
FIG. 3 shows a thermal desorption modulator.
Figure 3B:
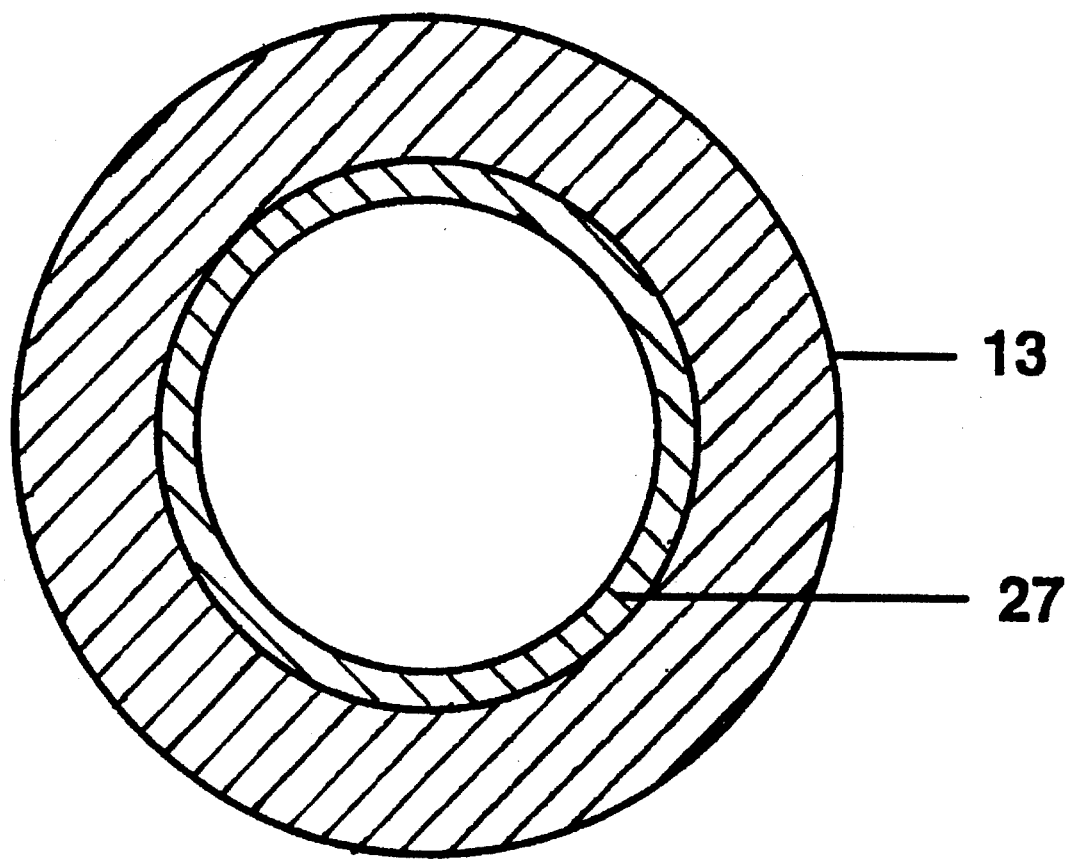

Referring to FIG. 3, for rapid and random cycling of cooling and heating a thermal column modulator circuit 31 is used consisting of power supply 32, for example 110V AC line, variable gain transformer 34, solid state relay 36, electrical ground 40 and injection signal 38. Heater 24 is connected to solid state relay 36. Referring to FIG. 3, electrical current from power supply 32 passing through heater 24 generates heat, causing tube 13 and sorbing phase 27 to heat. The temperature reached tube 13 and the sorbing phase 27 depends on the time that electrical power 32 is applied. When electrical power 32 is turned off, heater 24 cools. Cooling is rapidly due to the cooling effect of coolers 28.

Figure 4:
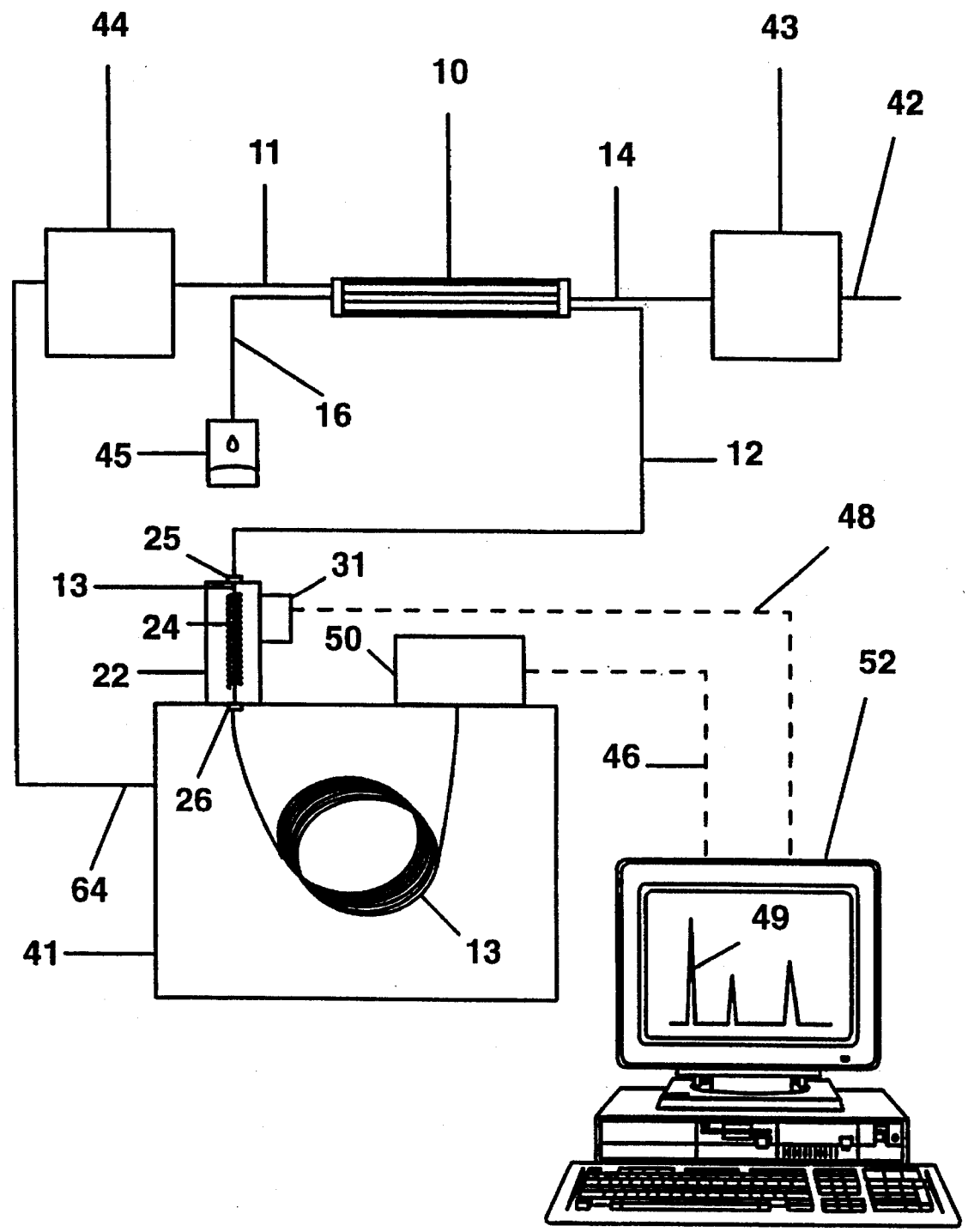
FIG. 4 shows a schematic for continuous extraction and analysis using a membrane module with cooling and heating.

Referring to FIG. 4, in one embodiment, thermal modulator 22 and circuit 31 are controlled by thermal modulator controller 48 from computer 52. Controller 48 may also be any device capable of switching power supply 32 and injection signal 38 on and off.

Referring further to FIG. 4, in operation, continuous solvent-free extraction and analysis of substances in fluid uses membrane module 10, thermal modulator 22, circuit 31 and a detector 50 which may be mounted on a chromatograph 41. Chromatograph 41 may be a gas chromatograph or supercritical fluid chromatograph for example. A pump 43 delivers solute fluid 42 which may be an analytical sample or municipal water flow, for example, through tube 14 and through membrane module 10 as previously described with reference to FIG. 2. A suitable pump 43 is a Spectra Physics Iso Chrom Liquid Chromatography Pump ( Spectra Physics, San Jose, Calif.) although any number of simple controlled flow and pressure pumps may be used. With further reference to FIG. 4, a source of extracting fluid 44, which may be a compressed gas such as nitrogen or a dense gas such as supercritical carbon dioxide enters membrane module 10 through tube 11. In one embodiment, extracting fluid is the carrier gas supply normally entering the gas chromatograph injection port. This carrier gas supply is disconnected from the gas chromatograph injection port and connected by connecting tube 64 directly to tube 11, by-passing extracting fluid source 44. Alternatively, extracting fluid is a source 44, for example, a cylinder of compressed gas such as nitrogen or a source of pressurized dense gas, such as a supercritial fluid pump connected a cylinder of suitable gas, such as carbon dioxide. Extracting fluid passing through tube 11 is a carrier to deliver extracted substances passing from solute fluid into extracting fluid through the semipermeable membrane 19 into tube 12. Tube 12 is connected to tube 13, which may be a gas chromatograph column by fitting 25. Extracted substances in extracting fluid passing through tube 12 into tube 13 are concentrated in sorbing phase 27 in tube 13 by cooling sorbing phase 27 in column tube 13 using cooling provided by thermal modulator 22. A substantially long cooling event followed by single rapid heating event constitutes a single injection. Alternatively, rapid and random pulses of cooling and heating may be used in a multiplex analysis. Extracted substances passing from sorbing phase 27, which may be the liquid phase of an open tubular capillary gas chromatographic column, are separated in the remainder of column 13 in gas chromatograph 41 and detected by detector 50. Detector 50 may be any one or combination of detectors, for example, flame ionization, electron capture, photoionization or mass spectrometer. Alternatively, tubing 12 containing sorbent 27 may be connected directly to detector 50 after passing through heater 24. This provides direct high sensitivity detection and analysis using a detector 50 such as mass spectrometer. Single chromatogram, single correlogram or mass spectrometry detector results 49 are displayed and analyzed by computer 52.

Figure 5:
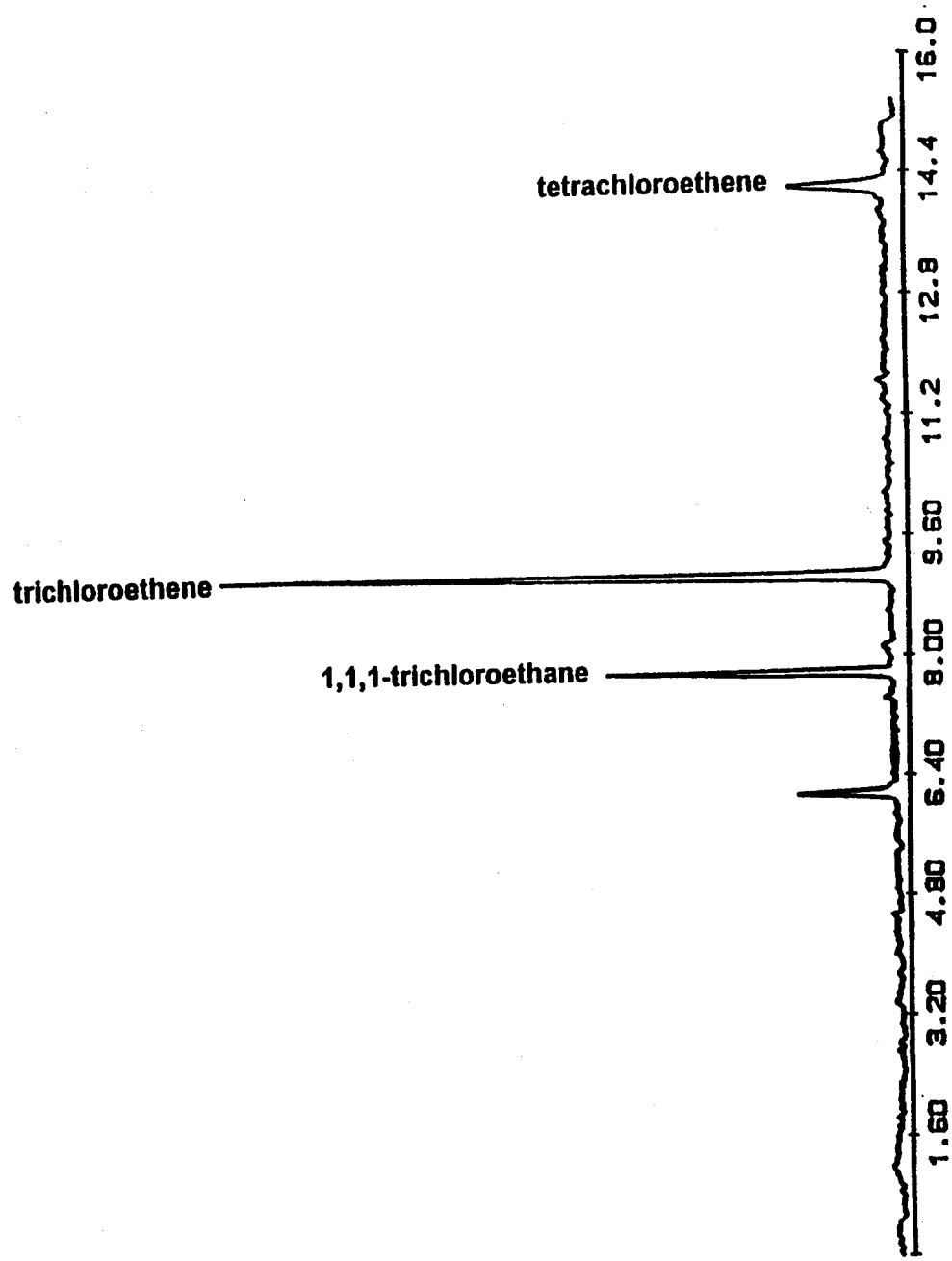
FIG. 5 shows a gas chromatogram of a single cool and heat cycle for extraction of volatile organics from water using a hollow fibre membrane module and direct connection to a chromatograph.

FIG. 5 is a single chromatogram result of the extraction and analysis of volatile organics from water using membrane module 10 with a straight 8.0 cm long, 100 micron inner diameter porous polypropylene hollow fibre membrane. A single cool and heat cycle is used. A spiked water solution containing 1,1,1-trichlorethane (268 µg/litre), trichloroethene ( 293 µg/litre) and tetrachloroethene( 325 µg/litre) is pumped through the membrane module. A DB-5 (J & W , Folson, Calif.) fused silica column 30 metres ×0.53 µm with 1.0 µm film thickness is used as the sorbant phase 27 and also acts as the gas chromatograph column 13. A detection limit of 30 µg/litre of water is estimated for a flame ionization detector. Sensitivity of the method would be enhanced by use of a more sensitive detector such as electron capture or ion trap mass spectrometer.

Figure 6:
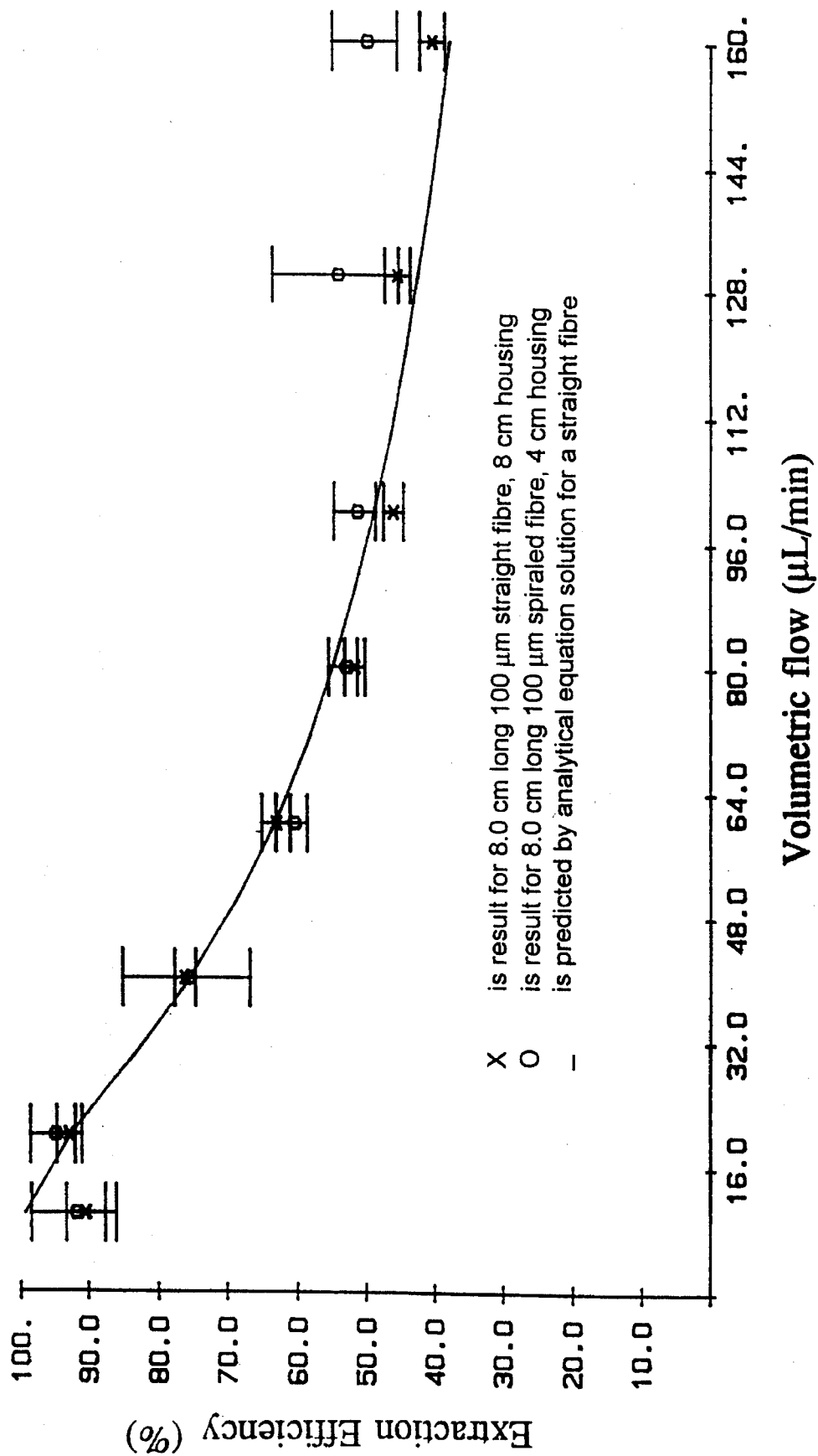
FIG. 6 shows a graph of results comparing the extraction efficiency of straight hollow fibre membrane to the extraction efficiency of spiralled hollow fibre membrane.

When using a hollow fibre membrane 19, extraction efficiency is increased by spiralling the membrane. This allows higher flow rates to be used without increasing the length of housing 20. FIG. 6 compares experimental results for volatile organics extraction using an 8.0 cm long straight hollow fibre tube extraction efficiency (*) to a 8.0 cm long spiralled fibre tube extraction efficiency (o) with nitrogen as the extraction fluid. The predicted result for the analytical solution to the diffusion equation for a straight fibre is shown for comparison (_) The length of housing 20 for the spiralled membrane was 4 cm and the length of the housing for the straight membrane was 8 cm. At low liquid flow rates there is essentially no difference between the two fibres. The flow is slow enough that volatile organics have sufficient time to diffuse from the solute fluid through the membrane and into the extracting fluid into the gaseous phase. At higher flow rates, the spiralled fibre exhibits greater extraction efficiency than the straight fibre. The improvement in extraction efficiency increases with an increase in the fibre diameter.

It is noted that increasing the volume of water passing through the membrane module for a given length of time increases the sensitivity and that lengthening the fibre increases the amount of solute extracted as does increasing the sampling time. These results agree with predictions from a semi-empirical model. The extraction rate for a nonporous silicone hollow fibre membrane is controlled by the diffusion of the solute in the solute phase.

With further reference to FIG. 4, continuous analysis of substances extracted using membrane module 10 from solute fluid 42 may be accomplished by using a modulation mode of detection. For example, using a Varian 3500 gas chromatograph 41 equipped with a flame ionization detector 50 ( Varian Instruments, Walnut Creek, Calif.), the carrier gas line leading into the injector of the gas chromatograph is disconnected and connected 64 to tube 11. Carrier gas for the gas chromatograph thereby becomes extracting fluid for the membrane module 10. Nitrogen can be used as the carrier gas for extraction. Any suitable gas chromatograph column 13 may be used for example, a DB-5 fused silica column 30 metres length with 0.53 mm internal diameter and a film thickness of 1 micron. A microcomputer 52 is used to provide the central control in an automated system for continuous analysis. A multiplex gas chromatograph process may be controlled by a Fortran or other suitable program. A binary random injection sequence is generated using a 10-stage feed back shift register. The sequence contains 2046 elements with a random period of 1023 elements. Two timed events are caused to occur simultaneously in the computer microprocessor 52 which contains a data acquisition board with direct memory access. Random injection signals 48 are sent out sequentially at a pre-defined frequency, which may be 1 Hz, through a parallel digital output channel to circuit 31 to control thermal modulator 22. Because reverse logic may be used, with reference to FIG. 3, when the injection signal 38 is at 0, an injection pulse 48 is sent to the solid state relay 36 and electrical current from power supply 32 is drawn from the variable gain transformer 34 to the heater 24. This creates a positive concentration pulse of substances from sorbent 27 in tube column tube 13. When the computer signal becomes negative, solid state relay 36 is off and the modulated section of tubing 13 containing sorbing phase 27, cools. Simultaneously, detector 50 output signal 46 is digitally sampled at the same frequency and stored into computer memory. System optimization for continuous analysis using a multiplex chromatograph system is possible by investigating gas chromatograph conditions, power supply level, heating pulse width and flowrate of solute fluid through membrane module 10. Cross correlation algorithm for multiplex calculation and feedback shift register technique for pseudorandom binary sequence generation are chosen for the multiplex program optimization based on computer simulation results. However, other transformation algorithms such as Hadamard transform and Fourier transform may be used.

Figure 7:
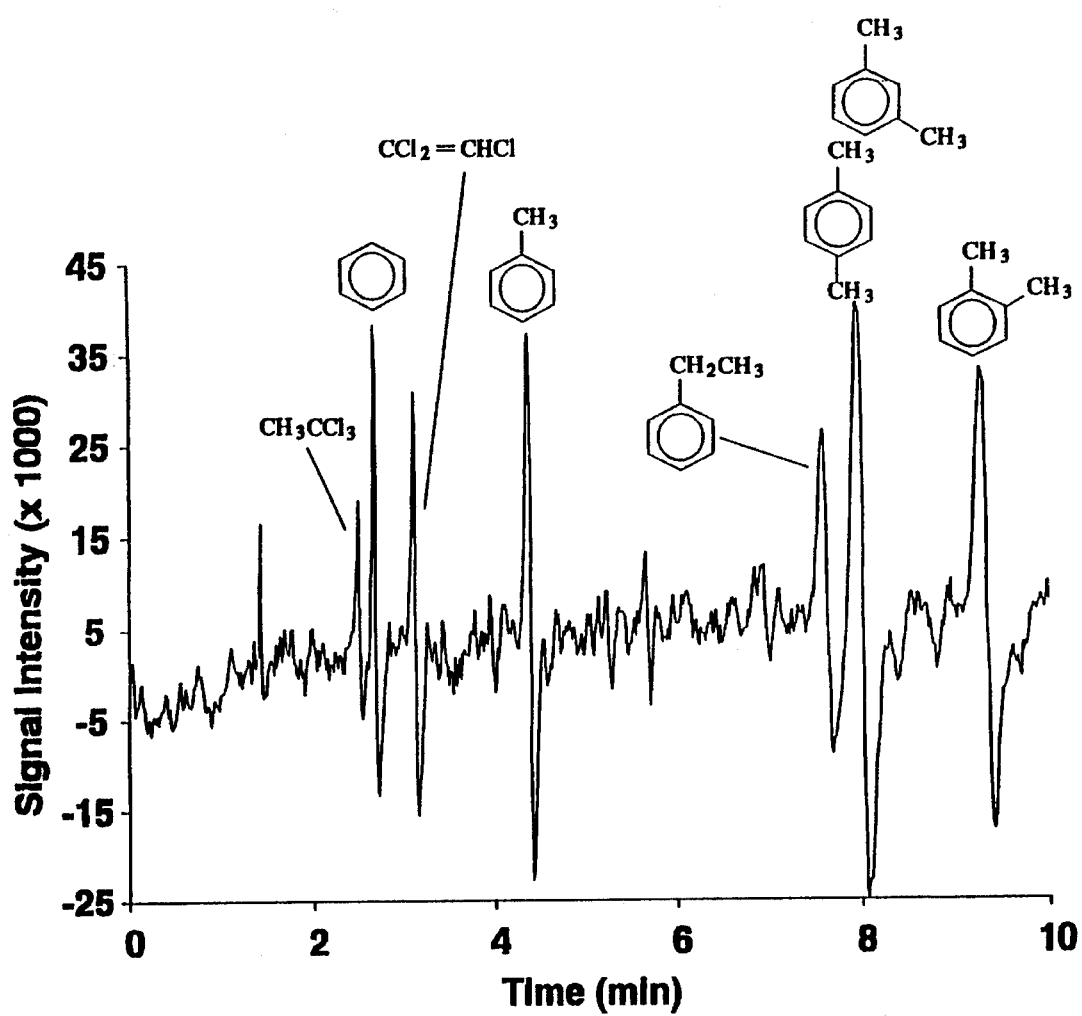
FIG. 7 shows a cross correlogram result from the continuous extraction and continuous analysis of volatile organic substances in water using a hollow fibre membrane module and multiplex gas chromatographic analysis.

FIG. 7 shows a cross correlogram result for the continuous extraction of organic pollutants in a spiked water sample. For the conditions studied, quantitative extraction and system linearity suitable for continuous extraction and analysis of varying samples is achieved. The invention is applicable for the continuous extraction and monitoring of organic substances in water treatment facilities. A clarified raw sewage sample obtained from the Burlington Skyway Municipal Sewage Treatment Plant in Burlington, Ontario was pumped continuously through the membrane module 10. An organic pollutant identified as toluene was determined directly in the sample by the continuous membrane extraction and continuous monitoring method at a level of 6.6 ug/litre. This result was confirmed using conventional batch liquid-liquid solvent extraction and gas chromatograph-mass spectrometer quantitation. This system could also be used for environmental safety monitoring of industrial effluent and in-plant process stream monitoring of organics in some process streams. Continuous monitoring of gaseous steams of the headspace streams generated by heating some solid samples is also possible.

For volatile substances and those with a Henry's law constant above 0.1, a gas such as nitrogen at relatively low pressures may be used as extracting fluid. However, for semi-volatile, non-volatile and polar substances an extracting fluid with very high solvating power, such as supercritical fluid, is used. Use of dense gas under pressure such as supercritical fluid carbon dioxide widens the volatility range of substances that may be continuously extracted. Since high pressures are required to produce supercritical fluid conditions, a high pressure membrane module is used.

Figure 8A:
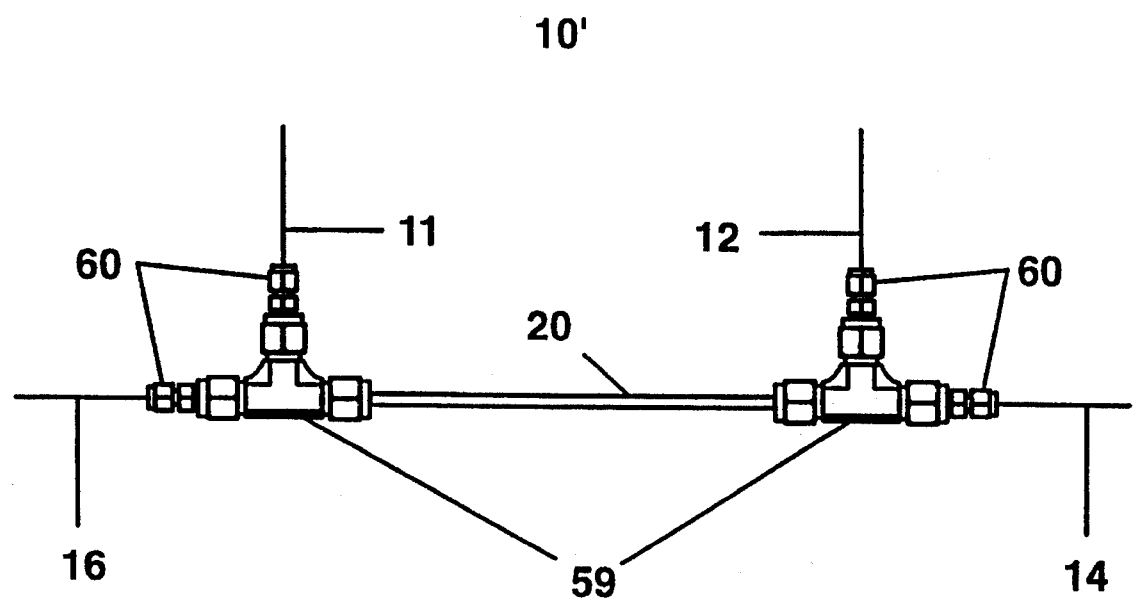
FIG. 8 shows a high pressure membrane module.
Figure 8B:
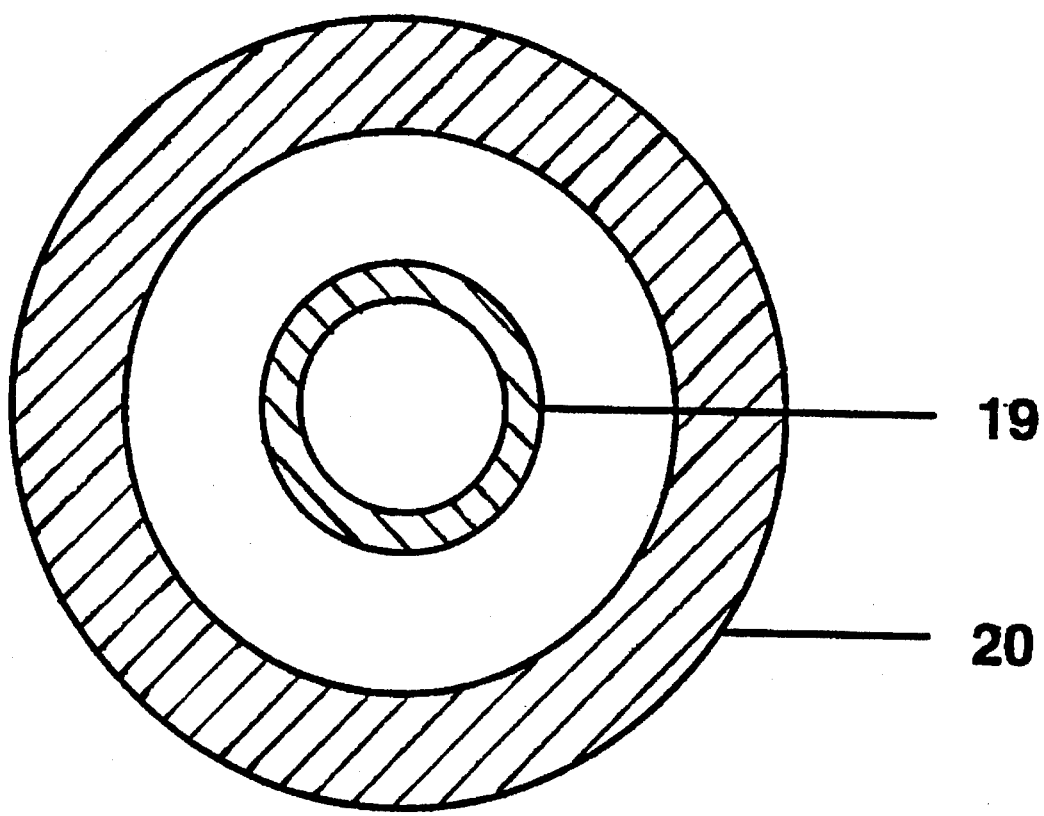
Figure 8C:
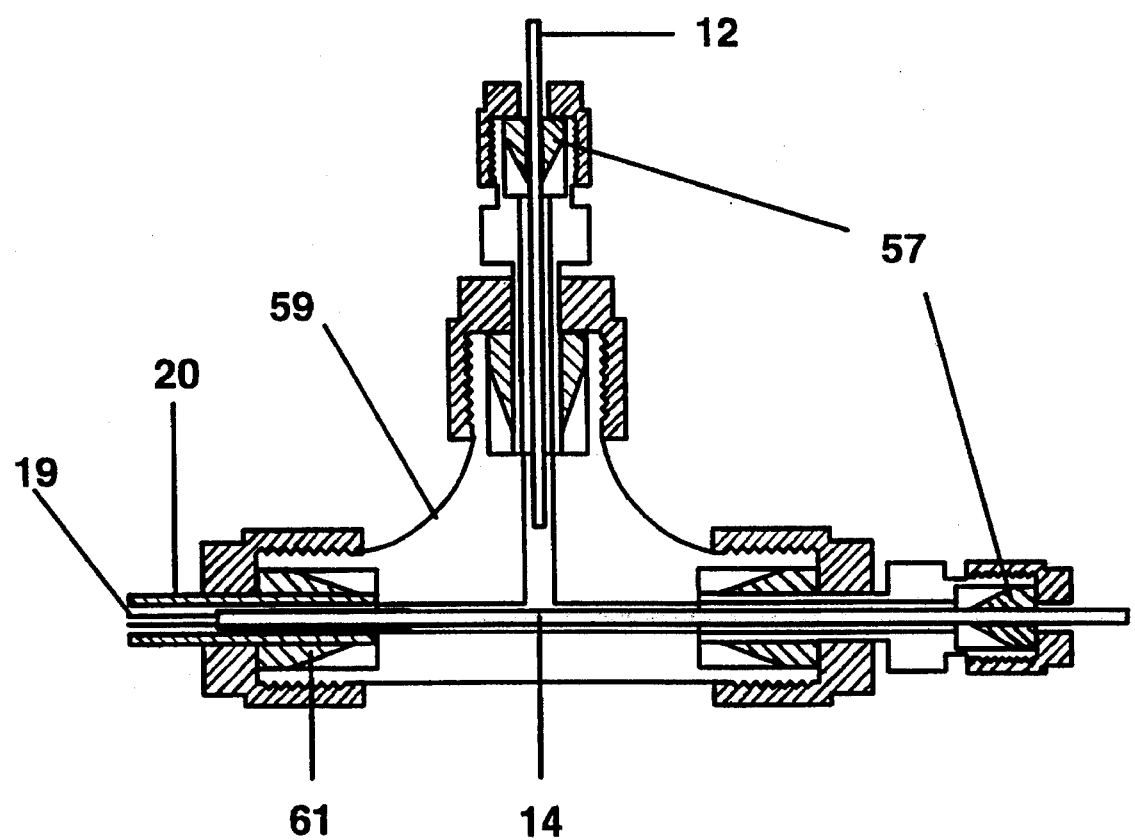

Referring to FIG. 8, a high pressure embodiment 10', of membrane module 10 consists of a housing 20, preferably a stainless steel tube although any housing capable of withstanding the pressure of dense gas or supercritical fluid, generally between 1500 psi and 10,000 psi, may be used. There are high pressure seals 59 for both ends of tube 20. Tubes 11 and 12 are inserted into seals and secured by ferrules 57 and fittings 60. Tube 14 and tube 16 are inserted substantially into each end of hollow fibre membrane 19 and inserted partially into each end of housing 20 and sealed in each opposing end of high pressure seal 59 by ferrules 61 and 57. An identical arrangement using end fitting 59 is used at both ends of tube 20. For tube 14 and tube 16, stainless steel needle tubing (Hamilton Co., Reno, Nev.) for example, may be used. Housing 20 is secured in end fitting 59 by ferrule 61. Fittings 60 may be used to attached tubes 11, 12, 14 and 16 to end fittings 59. In operation, solute fluid is pumped through tube 14 and passes into an interior surface of membrane 19. Extracting fluid, for example supercritical carbon dioxide, is pumped through tube 11 and into end fitting 59 and passes through between an exterior of membrane 19 and the interior of housing 20. Due to the high solvating power of pressurized dense gas as extracting fluid, semi-volatile, non-volatile and polar substances crossing semipermeable membrane 19 from solute fluid will be carried by extracting fluid through into tube 12. Tube 12 may also function as a restrictor for depressurization of extracting fluid. Alternatively, tube 12 may be connected to a suitable analysis device such as a supercritical fluid chromatograph to perform continuous analysis. Solute fluid, substantially depleted of volatile, semi-volatile and non-volatile substances after continuous extraction, passes through tube 16 which also functions as a restrictor to keep the pressure of the solute fluid within the membrane module on one side of membrane 19 substantially equal to the pressure of solvent fluid within the membrane module on the other side of membrane 19. For example this can be a 20 um inner diameter piece of fused silica tubing although various suitable fixed or variable restrictors may be used and this will vary depending on the pressure and flow rates used in the system.

Figure 9A:
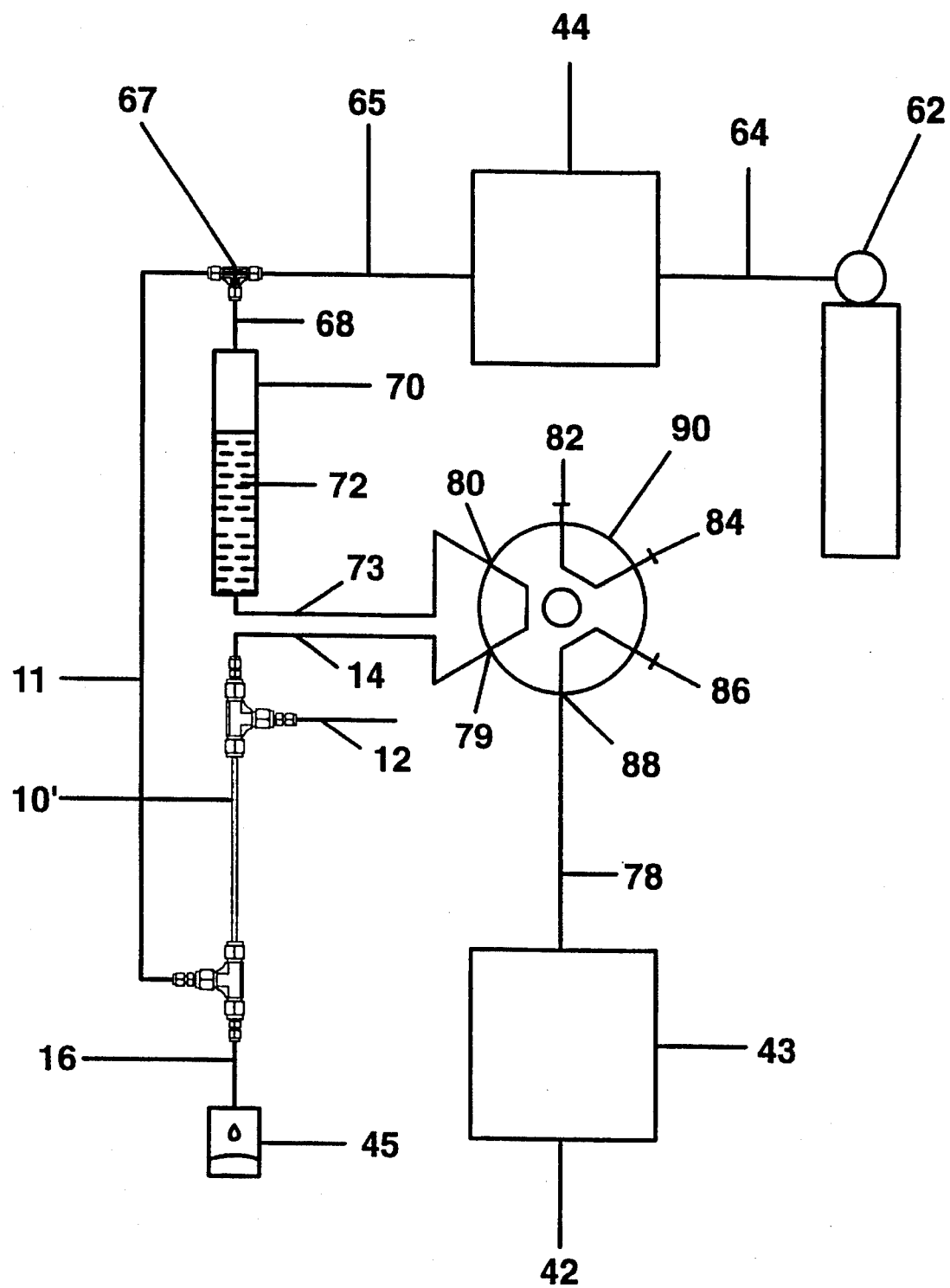
FIG. 9-A shows a schematic for pressurization before continuous extraction of substances in solute fluid using dense gas under pressure and a high pressure membrane module with two pumps.
Figure 9B:
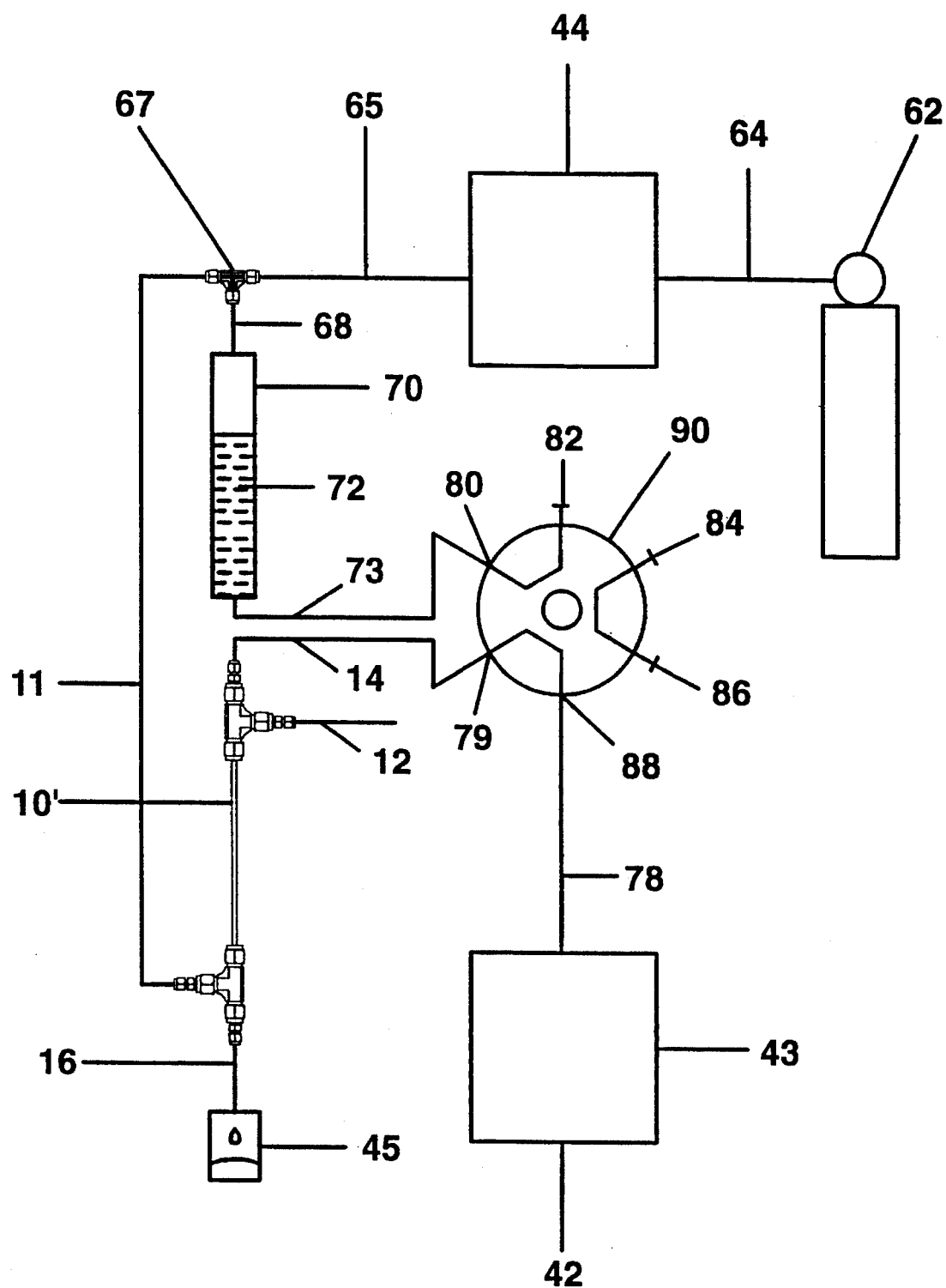
Figure 9C:
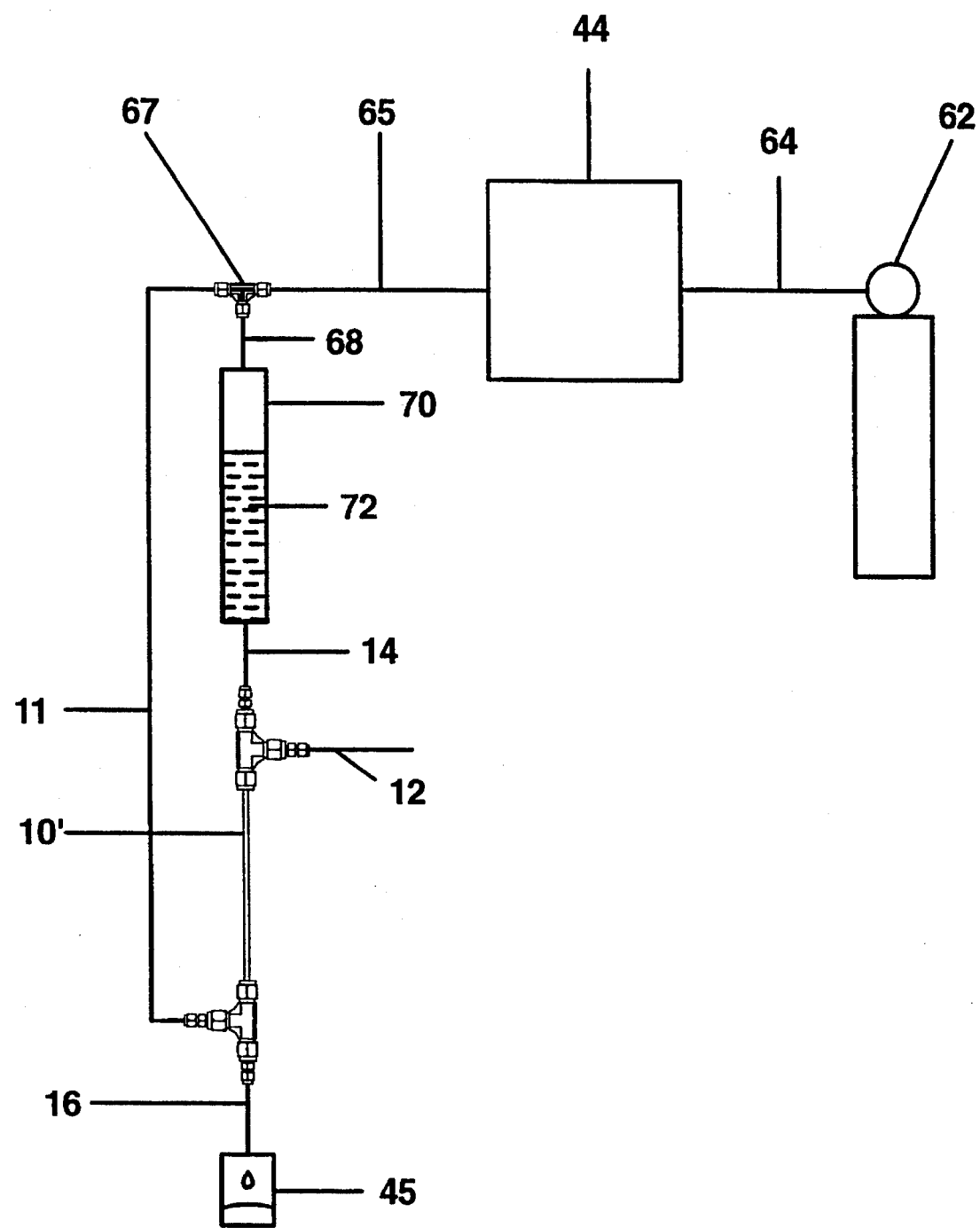

FIG. 9-A shows one possible embodiment of continuous extraction using pressurized dense gas. In this embodiment, system pressurization is achieved prior to continuous extraction using separate extracting fluid pump 44 and solute fluid pump 43. Pressurized dense gas is provided by a suitable pump 44 with connected by tubing 64 to a supply of extracting fluid 62. For example a cylinder of gas 62 such as carbon dioxide (Scott Gas, Plumstedville, Pa.) is connected to pump 44 such as an Isco Model 260D (Isco, Lincoln, Nebr.) supercritical fluid pump. Various other fluids may be used to generate dense gas, however carbon dioxide is suitable due to a low critical temperature and pressure. It is also non-toxic and inexpensive. To avoid damage due to pressure on membrane 19, the pressure on both sides of membrane 19 is maintained substantially equal. One way of achieving this is to provide pressurization of both sides of membrane 19 on startup, prior to extraction. For example, to accomplish this, a fluid reservoir 70, constructed of ¼" OD stainless steel tubing and two ¼" to ¹⁄₁₆" stainless steel reducers is connected to high pressure T fitting 67 using a short piece of stainless steel tubing 68. Reservoir 70 is substantially filled with a fluid 72 of similar viscosity to the solute fluid to be extracted. For example, for the extraction of groundwater as the solute fluid, distilled water may be used in reservoir 70. A 6-port high pressure valve 90 (Valco, Houston, Tex.) is used as a two position switching valve. Port positions 82, 84 and 86 of valve 90 are plugged with suitable stainless steel port plugs. Tubing 73 is connected to port 80. With valve 90 as in FIG. 6-A, ports 79 and 80 are connected through the valve. Port 79 is connected to one end of tubing 14. The other end of tubing 14 is connected into an interior surface of membrane 19 of membrane module 55 through end fitting 59 as shown in FIG. 8. Referring to FIG. 9-A, pressurized dense gas, for example supercritical carbon dioxide at 3000 psi from pump 44 passes through tube 65 and T fitting 67 into tubing 11. Simultaneously, pressurized dense gas enters reservoir 70 through tubing 68 causing fluid 72 under pressure to enter tube 73. With valve 90 in position as shown in FIG. 6-A, fluid under pressure 72 passes through ports 80 and 79 of valve 90 into tube 14 which enters into an interior of membrane 19. Simultaneously, extracting fluid under pressure enters through tube 16 into an exterior of membrane 19, thereby allowing the pressure to increase on both sides of membrane 19 in substantially equal manner.

Referring to FIG. 9-B, to perform extraction, valve 90 is switched and solute fluid 42, for example a groundwater sample or other fluid containing volatile, semi-volatile and non-volatile substances to be extracted, is pumped continuously by pump 43 through tube 78 and through ports 88 and 79 of valve 90 into tube 14, while reservoir fluid 72 under pressure is blocked at port 82. Pump 43 and restrictor tube 16 are adjusted such that the pressure in solute fluid is substantially equal to the pressure in extracting fluid passing through tube 68. To improve extraction consistency, by maintaining a constant relative flow rate of solute fluid and extraction fluid, pump 43 may incorporate a flow meter. Solute fluid is extracted as shown in FIG. 8. Extracted substances are carried by extracting fluid out of the high pressure membrane module $10^1$ by tube 12, which may also function as a restrictor for depressurization of extracting fluid, thus allowing collection of extracted substances for analysis. Alternatively, in an on-line system, tube 12 is connected to a suitable analysis device such as a supercritical fluid chromatograph.

Continuous extraction of solutes from a fixed volume reservoir 70 of solute fluid is also achieved with a variation of FIG. 9-B wherein valve 90 and pump 43 are eliminated. Referring to FIG. 9-C, in this embodiment, tube 14 is connected directly to reservoir 70 and tube 73 is eliminated. Solute fluid is used as fluid 70 in reservoir 72. Pressure is provided by pump 44 which causes solute fluid 72 in reservoir 70 to flow through tube 14 and to pass through the inside of hollow fibre membrane 19. Extraction fluid simultaneously passes though T-fitting 67 and tube 11 and enters membrane module 10' and passes between the inner wall of housing 20 and the exterior of membrane 19. Substances pass from the solute fluid through semipermeable membrane 19 and are carried by extraction fluid which passes out of the membrane module 10' through tube 12. This particular embodiment only requires the use of a single pump 63 and no valve is required. However, continuous extraction in this configuration is limited by the volume of solute fluid 72 contained in reservoir 70.

Due to the very high solvating power of pressurized dense gas, using extracting fluid such as supercritical carbon dioxide with the membrane module allows semi-volatile, non-volatile and polar substances such as organic acids, alcohols, phenols, pesticides, polychlorinated biphenyls, polynuclear aromatic hydrocarbons and dioxins to be removed from solute fluid such as water, using membranes in a continuous process.

FIG. 10 shows a table of results for extraction recoveries in the determination of two typical semi-volatile polar substances in United States Environmental Protection Agency Method 625. 2,4-dimethylphenol (DMP) and 2,4-dichlorophenol (DCP) are extracted at the 20 part per million level from water using a silicone hollow fibre membrane (Dow Corning, Mississauga, Ontario) and supercritical carbon dioxide at 3000 psi pressure. There is excellent agreement between the results obtained and theoretical modelling, which predict, for the conditions of water flow rate, inner diameter of fibre and fibre length used, an achievable theoretical extraction efficiency of 79.1%.

FIG. 8 represents one possible embodiment of a high pressure membrane extraction module. Many other variations are possible. For example a high pressure membrane module may be any housing designed to withstand pressures necessary for supercritical fluids, having a membrane 19 held in place and sealed by various other means other than end fittings 59 and needle tubing 58. Further, there is no theoretical limitation on size of the housing and high pressure membrane extraction is therefore not limited to analytical scale continuous extraction using dense gas under pressure but will be useful for various process scale applications and purification procedures.

The present invention has several advantages over the prior art. For example, the process is continuous and the membrane is used with supercritical fluids. The membrane can be chosen so that it is selective of certain components in the solute fluid and does not permit all of the components of the solute fluid to be extracted by the extracting fluid.

What I claim as my invention is:

1. A device for continuous extraction and analysis of one or more substances in a solute fluid, said device comprising a semipermeable structure in a housing and a sorbing phase in combination, said solute fluid passing on one side of said semipermeable structure and an extracting fluid simultaneously passing on the other side of said semipermeable structure, said extracting fluid constituting carrier means to deliver said substances passing from said solute fluid through said semipermeable structure into said extracting fluid, said extracting fluid passing through said sorbing phase, with means to cool said sorbing phase to adsorb said substances from said extracting fluid, with means to heat said sorbing phase to desorb said substances into said extracting fluid to increase concentration of said substances in said extracting fluid, said extracting fluid passing directly from said sorbing phase to an analysis device.

2. A device as claimed in claim 1 wherein said substances are organic compounds.

3. A device as claimed in claim 1 wherein said semipermeable structure is a flat semipermeable membrane.

4. A device as claimed in claim 1 wherein said semipermeable structure is a hollow fibre membrane.

5. A device as claimed in claim 1 wherein said semipermeable structure is a spiralled hollow fibre membrane.

6. A device as claimed in claim 1 wherein said extracting fluid is a gas or pressurized dense gas.

7. A device as claimed in claim 1 wherein said analysis device is a chromatograph.

8. A device as claimed in claim 1 wherein said analysis device is a mass spectrometer.

9. A device as claimed in claim 1 wherein said semipermeable structure, said sorbing phase and said analysis device are connected directly to one another in series.

10. A device as claimed in claim 1 wherein said analysis device is changing the composition of said extracting fluid containing said substances by a thermal decomposition or an electrochemical reaction or a photochemical reaction.

11. A device as claimed in claim 1 wherein said sorbing phase consists of a solid sorbent such as carbon or a liquid sorbent such as polydimethysilicone or a selective sorbent such as silver oxide.

12. A device as claimed in claim 1 wherein said sorbent is a portion of a chromatographic column.

13. A process for continuous separation and analysis of one or more substances in a solute fluid using a semipermeable structure in a housing, a sorbing phase with heating and cooling means, and an analysis device, said sorbing phase being connected between said housing and said analysis device, said process comprising:

(a) passing said solute fluid passing on one side of said semipermeable structure;

(b) passing an extracting fluid simultaneously through said housing on another side of said semipermeable structure;

(c) delivering said substances passing from said solute fluid through said semipermeable structure to said sorbing phase using said extracting fluid as carrier means for said substances, passing said extracting fluid out of said housing to said sorbing phase, cooling said sorbing phase to adsorb said substances from said extracting fluid, then heating said sorbing phase to desorb said substances from said sorbing phase to said extracting fluid to increase concentration of said substances in said extracting fluid, there being no chemicals added; and (d) passing said extracting fluid to said analysis device and analyzing said substances.

14. A process as claimed in claim 13 wherein said semipermeable structure is selected from the group of a flat semipermeable membrane, a hollow fibre membrane and a spiralled hollow fibre membrane.

15. A process as claimed in claim 13 wherein said sorbing phase is selected from the group of graphitized carbon, glass beads, styrenedivinylbenzene, polydimethylsiloxane and silver oxide impregnated silica.

16. A process as claimed in claim 13 wherein said cooling and heating of said sorbing phase includes a single cooling for a substantially long period of time followed by a single heating for a substantially short period of time.

17. A process as claimed in claim 13 wherein said cooling and heating is performed as cycles with a high repetition rate and random sequence.

* * * * *